US008609891B2

(12) United States Patent
Bae et al.

(10) Patent No.: US 8,609,891 B2
(45) Date of Patent: Dec. 17, 2013

(54) PHOTOACID GENERATORS AND PHOTORESISTS COMPRISING SAME

(75) Inventors: Young Cheol Bae, Weston, MA (US); Thomas Cardolaccia, Needham, MA (US); Yi Liu, Wayland, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 103 days.

(21) Appl. No.: 13/095,533

(22) Filed: Apr. 27, 2011

(65) Prior Publication Data

US 2011/0287361 A1   Nov. 24, 2011

Related U.S. Application Data

(60) Provisional application No. 61/328,608, filed on Apr. 27, 2010.

(51) Int. Cl.
| | | |
|---|---|---|
| G03F 7/004 | (2006.01) | |
| G03F 7/028 | (2006.01) | |
| G03F 7/26 | (2006.01) | |
| C07C 309/04 | (2006.01) | |
| C07C 309/06 | (2006.01) | |
| C07C 309/13 | (2006.01) | |

(52) U.S. Cl.
USPC ........ 562/109; 562/113; 430/270.1; 430/921; 430/925

(58) Field of Classification Search
USPC .............. 430/270.1, 326, 919, 920, 921, 923, 430/925, 322; 562/100, 105, 113, 115, 108
See application file for complete search history.

(56) References Cited

U.S. PATENT DOCUMENTS

| | | | | |
|---|---|---|---|---|
| 4,885,158 | A | * | 12/1989 | Tracy et al. ............... 424/69 |
| 6,455,226 | B1 | | 9/2002 | Lee et al. |
| 2002/0091216 | A1 | | 7/2002 | Lee et al. |
| 2002/0102491 | A1 | * | 8/2002 | Kodama et al. ............ 430/270.1 |
| 2002/0155383 | A1 | * | 10/2002 | Fujimori et al. ........... 430/282.1 |
| 2004/0087690 | A1 | | 5/2004 | Lamanna et al. |
| 2008/0206671 | A1 | * | 8/2008 | Thackeray et al. ........ 430/270.1 |
| 2010/0136479 | A1 | * | 6/2010 | Yamaguchi et al. ....... 430/270.1 |
| 2010/0304303 | A1 | * | 12/2010 | Maeda et al. .............. 430/286.1 |

FOREIGN PATENT DOCUMENTS

| | | | |
|---|---|---|---|
| EP | 0 401 499 A1 | | 12/1990 |
| EP | 1574903 A1 | | 9/2005 |
| JP | 60-004165 | * | 1/1985 |
| WO | WO 2009/057769 | * | 5/2009 |
| WO | 2011104127 A1 | | 9/2011 |

OTHER PUBLICATIONS

English Translation of Chinese Office Action issued in connection with corresponding Chinese Patent Application No. 201110187346.3, Mar. 12, 2013.
European Search Report issued Sep. 6, 2011 for corresponding European Patent Application No. 11163651.0.
European Search Report issued Dec. 28, 2011 for corresponding European Patent Application No. 11163651.0.

* cited by examiner

*Primary Examiner* — Anca Eoff
(74) *Attorney, Agent, or Firm* — Peter F. Corless; Edwards Wildman Palmer LLP; Darryl P. Frickey

(57) ABSTRACT

New photoacid generator compounds are provided that comprise a nitrogen-base functional component of the structure —C(=O)N<. Photoresist compositions also are provided that comprise one or more PAGs of the invention.

20 Claims, No Drawings

PHOTOACID GENERATORS AND PHOTORESISTS COMPRISING SAME

This application claims the benefit of priority under 35 U.S.C. §119(e) to U.S. Provisional Application No. 61/328,608, filed Apr. 27, 2010, the entire contents of which application are incorporated herein by reference.

This invention relates to new photoacid generator compounds ("PAGs") and photoresist compositions that comprise such PAG compounds. In particular, the invention relates ionic PAGs that comprise a moiety of the structure —C(=O)N< such as a lactam, amide or imide. Preferred photoacid generator are salts where the anion component comprises comprise a moiety of the structure —C(=O)N< such as a lactam, amide or imide.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. Nos. 6,664,022 and 6,849,374.

In one aspect, the invention provides new photoacid generator compounds (PAGs) that comprise a nitrogen-base functional component of the structure —C(=O)N<. Preferably, such moieties can function as a hydrogen-bond acceptor. As referred to herein, with respect to the structure —C(=O)N<, the nitrogen valences (i.e. < represent separate linkages independent may be linked to either hydrogen or a non-hydrogen substituent.

In a preferred aspect, photoacid generator compounds of the invention comprise a non-cyclic amide moiety.

In another preferred aspect, photoacid generator compounds of the invention comprise a lactam moiety.

In another preferred aspect, photoacid generator compounds of the invention comprise an imide moiety.

In a particularly preferred aspect, photoacid generator compounds comprise an anionic component that comprise a structure —C(=O)N<. such as a lactam, amide or imide. For instance, a preferred anion component comprise a sulfonic acid ($SO_3^-$) group which may have optionally substituted alkyl substitution, e.g. a fluoroalkyl group that is substituted with a structure —C(=O)N<. such as a lactam or non-cyclic amide or an imide.

Preferred lactam moieties of photoacid generator compounds of the invention include e.g. piperidinonyl and pyrrolidinonyl groups In another aspect, photoresist compositions are provided that comprise one or more photoacid generator compounds as disclosed herein. Preferably, a photoresist composition comprises one or more components that can hydrogen-bond or otherwise complex with the —C(=O)N<. PAG structure. For instance, preferred are photoresist compositions that comprise a resin component that contain acrylic acid units (which may result from a photoacid-induced deprecation reaction). Such acidic groups can hydrogen bond with the —C(=O)N< PAG structure.

Without being bound by any theory, it is believed that PAGs of the invention can minimize undesired photoacid diffusion into unexposed photoresist regions. That is, the photoacid-generated acid with basic —C(=O)N<. structure can complex with acidic groups such as deprotected carboxylic acid group of a resist photoacid-labile resin component. Such complexing of the PAG can effectively localize and restrict the activated PAG to exposed resist regions and largely preclude undesired diffusion of photoacid into unexposed resist regions.

Additionally, again while not being bound by any theory, an unactivated photoacid generator compound of the present invention with a basic —C(=O)N<. structure as present in unexposed regions can function as an effective quencher molecule and restrict diffusive migration of photogenerated acid into unexposed resist regions. In distinction, in exposed photoresist regions, the photoactivated PAG will be effectively acidic for activation of the resist (e.g. to catalyze deblocking reactions of a resin component with photoacid-labile groups) notwithstanding the basic —C(=O)N< PAG moieties.

Thus, PAGs of the invention can impart enhanced contrast and resolution between exposed and unexposed photoresist composition layer regions as a result of several independent phenomena.

PAGs of the invention may be suitably used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Preferred imaging wavelengths of photoresists of the invention include sub-300 nm wavelengths e.g. 248 nm, and sub-200 nm wavelengths e.g. 193 nm and EUV.

Particularly preferred photoresists of the invention contain an imaging-effective amount of one or more PAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624 incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083.

Resists of the invention also may comprise a mixture of distinct PAGs, typically a mixture of 2 or 3 different PAGs, more typically a mixture that consists of a total of 2 distinct PAGs.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

As discussed above, we now provide photoacid generator compounds (PAGs) that comprise a nitrogen-base functional component of the structure —C(=O)N<.

As discussed above, as referred to herein, with respect to the structure —C(=O)N<, the nitrogen valences (i.e. < represents separate linkages independent may be linked to either hydrogen or a non-hydrogen substituent, and the carbonyl valence, i.e. —C(=O)N< is a linkage to the balance of the PAG compound. Thus, the structure —C(=O)N< also could be depicted as —C(=O)N(R)($R^1$) where R and $R^1$ are the same or different and are hydrogen or a non-hydrogen substituent such as optionally substituted alkyl including optionally substituted $C_{1-30}$alkyl, optionally substituted including $C_{3-30}$ cycloalkyl, optionally substituted alkoxy including optionally substituted $C_{1-30}$alkoxy, optionally substituted carbocyclic including $C_{6-30}$ carbocyclic group, optionally substituted heteroalicyclic including $C_{3-30}$ heteroalicyclic that contains 1, 2 or 3 N, O and/or S ring atoms, and the like.

Particularly preferred PAGs of the invention comprise 1) a $SO_3^-$ moiety; 2) a structure —C(=O)N<; and 3) one or more fluorinated carbons (e.g. one or more —$CF_2$—, —CHF—). In certain preferred aspects, one or more of the fluorinated carbons either directly or indirectly is substituted by an ester keto group (e.g. —C(=O)OR where R is a hydrogen or preferably non-preferably substituent) and/or the structure —C(=O)N<. A fluorinated carbon is indirectly substituted by an ester keto group e.g. —C(=O)OR and/or —C(=O)N< where non-fluorinated carbons and/or hetero atoms are interposed between the fluorinated carbon and the ester keto group, and fluorinated carbon is directly substituted by an ester keto group (e.g. —C(=O)OR) and/or —C(=O)N<. where no non-fluorinated carbons and/or hetero atoms are interposed between the fluorinated carbon and the ester keto group. In many aspects, it is preferred that a fluorinated carbon is indirectly substituted by an ester keto group and/or —C(=O)N<.

In particularly preferred aspect, preferred are PAGs that comprise both (1) an ester keto group (e.g. —C(=O)OR where R is as defined above) and (2) —C(=)N<.

In a related but separate aspect, preferred are PAGs that comprise one or more fluorinated carbons (including difluorocarbons) (e.g. —$CHF_2$—, —$CF_2$—), particularly where a —$CF_2$— moiety is directly bonded to a $SO_3^-$ moiety i.e. —$CF_2$—$SO_3^-$.

Particularly preferred photoacid generator compounds of the invention may comprise a structure of the following formula (I):

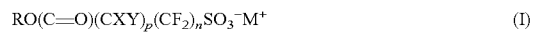

$$RO(C=O)(CXY)_p(CF_2)_nSO_3^-M^+ \qquad (I)$$

wherein R is non-hydrogen substituent that comprises a group of the structure —C(=O)N($R^1$)($R^2$) where $R^1$ and $R^2$ are each the same or different and may be hydrogen or a non-hydrogen substituent such as optionally substituted alkyl including optionally substituted $C_{1-30}$alkyl, optionally substituted including $C_{3-30}$ cycloalkyl, optionally substituted alkoxy including optionally substituted $C_{1-30}$alkoxy, optionally substituted carbocyclic including $C_{6-30}$ carbocyclic group, optionally substituted heteroalicyclic including $C_{3-30}$ heteroalicyclic that contains 1, 2 or 3 N, O and/or S ring atoms, and the like, where preferably one or both $R^1$ and $R^2$ are other than hydrogen, or $R^1$ and $R^2$ may be taken together to form a ring with the nitrogen e.g. a lactam structure such as an optionally substituted piperidinonyl moiety or optionally substituted pyrrolidone moiety, or an imide or amide structure;

X and Y are each independently hydrogen or a non-hydrogen substituent such as halo (particularly fluoro), cyano, nitro, or a non-hydrogen substituent as set forth above for R;

p is 0 or a positive integer, and preferably p is 1, 2 or 3;

n is a positive integer and preferably is 1, 2 or 3, more preferably 1 or 2;

M+ is a counter ion, and preferably is an organic onium salt component, such as a sulfonium or iodonium cation component, particularly a trisubstituted sulfonim cation or a disubstituted iodonium cation.

In the above Formula (I), suitably one or more (e.g. 1 to 10) carbon or hetero atoms are interposed between the group —C(=O)N($R^1$)($R^2$) and O(C=O)(CXY)$_p$(CF$_2$)$_n$SO$_3^-$M$^+$., i.e. the group R in Formula (I) may be —(CXY)$_{1-10}$C(=O)N($R^1$)($R^2$) where each occurrence of X and Y is independently independently hydrogen or a non-hydrogen substituent such as halo (particularly fluoro), cyano, nitro, or a non-hydrogen substituent as set forth above for R in Formula (I)

In certain aspects, anion components of preferred ionic PAGs of the invention may comprise a structure of the following Formulae (I) through (XV):

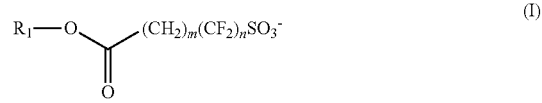

(I)

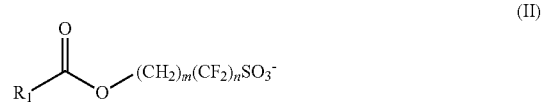

(II)

(III)

-continued
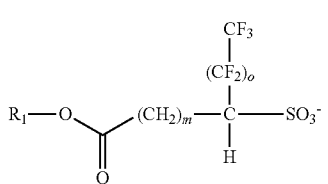 (IV)
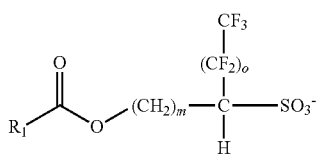 (V)
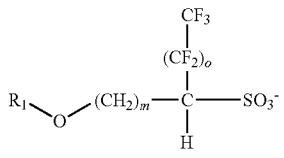 (VI)
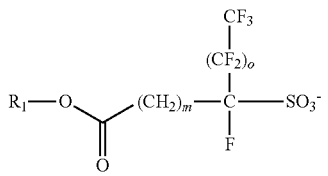 (VII)
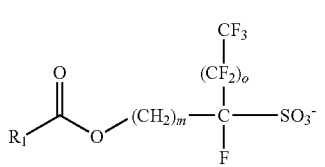 (VIII)
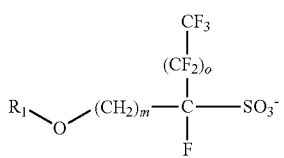 (IX)
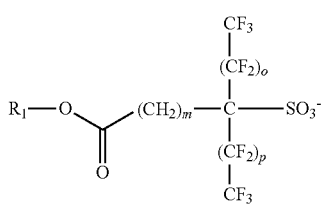 (X)
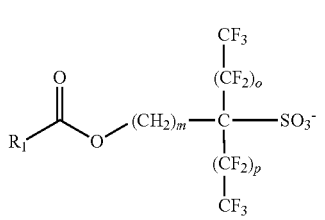 (XI)
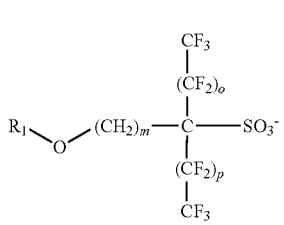 (XII)
-continued
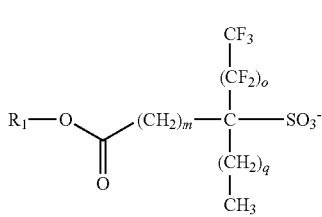 (XIII)
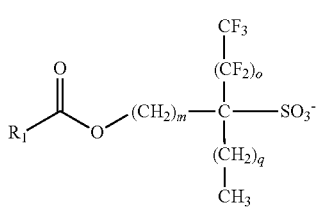 (XIV)
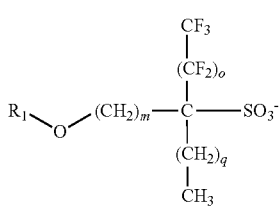 (XV)
wherein in each of Formulae (I) to (XV):
m, n, o, p, q are independently an integer of 0 to 10;
$R_1$ is one of the group (A), (B), (C), (D), (E), or (F) below:
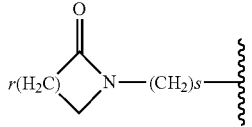 (A)
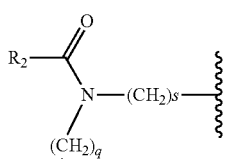 (B)
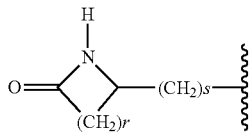 (C)
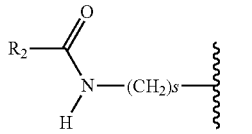 (D)
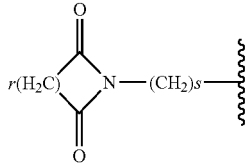 (E)

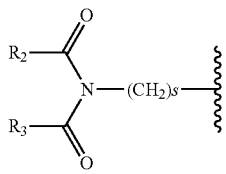

(F)

wherein:

$R_2$ and $R_3$ are independently branched, non-branched or cyclic aliphatic group such as optionally substituted alkyl including optionally substituted $C_{1-30}$alkyl, optionally substituted including $C_{3-30}$ cycloalkyl, optionally substituted alkoxy including optionally substituted $C_{1-30}$alkoxy, optionally substituted carbocyclic including $C_{6-30}$ carbocyclic group, optionally substituted heteroalicyclic including $C_{3-30}$ heteroalicyclic that contains 1, 2 or 3 N, O and/or S ring atoms;

q and r are independently an integer from 0 to 10;

s is a positive integer from 1 to 10.

Such anion components of Formulae (I) through (XV):are suitably complexed with a cation counter ion, such as discussed above $M^+$ above, i.e. an organic onium salt component, such as a sulfonium or iodonium cation component, particularly a trisubstituted sulfonim cation or a disubstituted iodonium cation.

As stated herein above, various substituent groups of PAGs of the invention may be optionally substituted. Substituted moieties are suitably substituted at one or more available positions by, e.g., halogen such as F, Cl Br and/or I, nitro, cyano, sulfono, alkyl including $C_{1-16}$ alkyl with $C_{1-8}$ alkyl being preferred, haloalkyl such as fluoroalkyl (e.g. trifluoromethyl) and perhaloalkyl such as perfluoro$C_{1-4}$alkyl, alkoxy including $C_{1-16}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, alkoxy groups of PAG compounds of the invention have one or more oxygen linkages, typically 1 to about 5 or 6 oxygen linkages. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazole.

Photoacid generator compounds of the invention may be readily produced. Exemplary syntheses are set forth in the examples which follow. For instance, a compound that comprises an acid moiety such as a sulfonic acid moiety is treated with base and then coupled with a compound comprising a structure —C(═O)N< such as a lactam, amide or imide. The coupled compound comprising both acid and structure —C(═O)N< then can be acidic and joined with a counter ion such as a sulfonium or iodonium cation. Synthesis of a particularly preferred PAG of the invention is set forth in Example 1 which follows.

As discussed above, PAGs of the invention are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

PAGs of the invention also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 10 or 5 mole or weight percent aromatic groups, more preferably less than about 1 or 2 mole or weight percent aromatic groups, more preferably less than about 0.1, 0.02, 0.04 and 0.08 mole or weight percent aromatic groups and still more preferably less than about 0.01 mole or weight percent aromatic groups. Particularly preferred polymers are completely free of aromatic groups. Aromatic groups can be highly absorbing of sub-200 nm radiation and thus are undesirable for polymers used in photoresists imaged with such short wavelength radiation. In certain preferred aspects, the photoresist polymers may be contain less than about 10 or 5 mole percent aromatic groups other than naphthyl groups (particularly other than hydroxynaphthyl groups), more preferably less than about 1 or 2 mole percent aromatic groups other than naphthyl groups (particularly other than hydroxynaphthyl groups). In such preferred systems, the photoresist polymers may comprise a significant amount of naphthyl groups (particularly hydroxynaphthyl groups) e.g. at least 1, 5, 10, 15, 20, 25, 30, 35, 40 or 45 mole or weight percent of the polymer may be comprised of naphthyl groups (particularly hydroxynaphthyl groups).

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamanatylacrylate, methyladamanylmethacrylate, ethylfencylacrylate, ethylfencylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, sensitizers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm². As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The following non-limiting examples are illustrative of the invention.

EXAMPLE 1

PAG Synthesis—Synthesis of Triphenylsulfonium (1-pyrrolidonemethoxycarbonyl)-difluoromethanesulfonate Scheme 1:

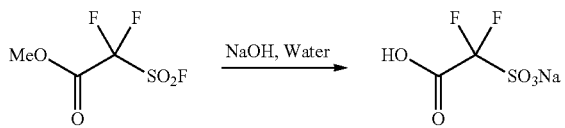

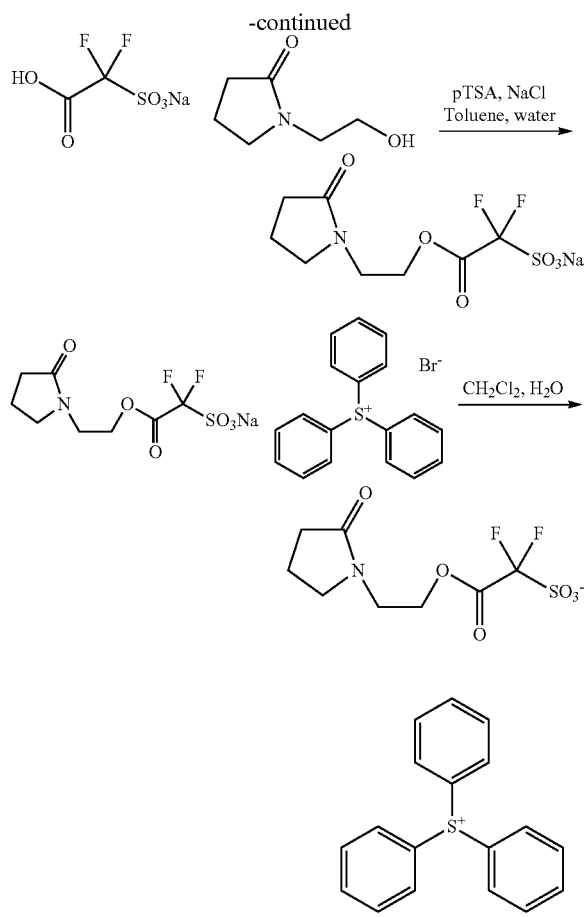

The title compound, triphenylsulfonium (1-pyrrolidonemethoxycarbonyl)-difluoromethanesulfonate was prepared as depicted in Scheme 1 above and as follows: Sodium hydroxide (6.400 g, 160 mmol) was placed in a 100 mL round-bottom flask fitted with a condenser and water (30 mL) was added. The suspension was stirred magnetically for 30 min, then cooled down to 0° C. with an ice-bath. Methyl-2, 2-difluoro-2-(fluorosulfonyl)acetate (9.605 g, 50 mmol) was added dropwise over 15 min. When the addition was complete, the mixture was left stirring under reflux for 18 hours. After this time, the mixture was cooled down to room temperature, filtered on a Buchner funnel to remove salts and the filtrate was acidified to pH=2 with aqueous HCl. The water was then removed under reduced pressure at 55° C. to give a colorless oil of sodium carboxydifluoromethanesulfonate. The next step was carried out assuming 100% conversion. $^{13}$C NMR (125 MHz, D$_2$O) δ 113.69 (t), 165.53; $^{19}$F NMR (282 MHz, D$_2$O) δ −108.83

Sodium carboxydifluoromethanesulfonate obtained from the previous step, 1-(2-hydroxyethyl)pyrrolidin-2-one (9.687 g, 75 mmol), para-toluenesulfonic acid monohydrate (19.020 g, 100 mmol) and sodium chloride (8.766 g, 150 mmol) were placed in a 250 mL three neck round-bottom flask fitted with a condenser and mechanical stirrer. Toluene (200 mL) and water (12.5 mL) were added and the suspension was rapidly stirred under strong reflux for 2 hours. A Dean-Starck trap was then placed between the flask and the condenser and the suspension was left stirring under strong reflux overnight. After this time, the suspension was brought to room temperature, the solids were filtered off on a Buchner funnel, washed with toluene and air-dried. The solids were suspended in acetonitrile (100 mL), stirred at room temperature for 30 min, insoluble materials were filtered off on a Buchner funnel, and washed with acetonitrile. The solvent was removed under reduced pressure from the filtrate to give a white-orange solid. $^{19}$F NMR of the crude intermediate product obtained indicates a conversion of 79.9% at this stage. The solid was then placed in a 250 mL round-bottom flask and triphenylsulfonium bromide (13.710 g, 39.95 mmol), dichloromethane (120 mL) and water (120 mL) were added. The suspension was stirred magnetically at room temperature overnight. The suspension was then placed in a separatory funnel and the organic phase was washed with water (5×100 mL). Activated carbon (5 g) was added to the organic phase, stirred for 10 min and the solid filtered off. The organic phase was dried with magnesium sulfate and the solvent removed under reduced pressure to give a colorless oil. The oil was diluted with acetone (20 mL) and ethyl acetate was added slowly (250 mL). After 3 days in the freezer, a white crystalline solid was collected on a Buchner funnel, washed with cold ethyl acetate, air-dried and finally dried under vacuum at 40° C. for 24 h. Yield=4.32 g (16% overall). $^1$H NMR (500 MHz, Acetone-D$_6$): δ 7.95 (d, 6H), 7.90 (t, 3H), 7.83 (t, 6H), 4.30 (t, 2H), 3.50 (m, 4H), 2.16 (t, 2H), 1.91 (m, 2H); $^{13}$C NMR (125 MHz, Acetone-d$_6$): δ 172.5, 161.8, 161.5, 135.5, 132.4, 132.3, 126.0, 65.3, 48.6, 41.8, 31.0, 18.9 $^{19}$F NMR (282 MHz, Acetone-d$_6$) δ −110.3;

EXAMPLE 2

Polymer Synthesis: Synthesis of poly(MAMA/α-GBLMA/ODOTMA/HAMA)

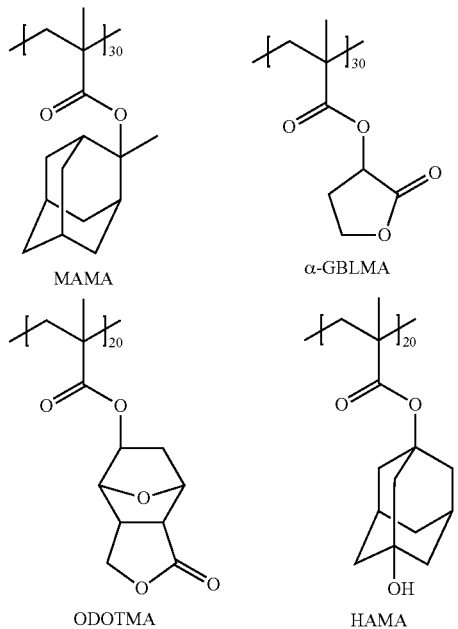

The title polymer is prepared as follows and is a useful resin components of a positive-acting chemically amplified photoresist of the invention.

16.25 g of MAMA, 11.80 g of α-GBLMA, 11.07 g of ODOTMA and 10.92 g of HAMA were dissolved in 48 g of THF. The mixture was degassed by bubbling with nitrogen for 20 min. A 500 ml flask equipped with a condenser, nitrogen inlet and mechanical stirrer was charged with 18 g of THF and the solution brought to a temperature of 67° C. 4.87 g of V601 (dimethyl-2,2-azodiisobutyrate, 9.15 mol % a with respect to monomers) was dissolved in 5 g of THF and charged into the flask. The monomer solution was fed into the reactor at a rate of 28.57 mL/h. The monomer feeding was carried out for 3 hours 30 min. After monomer feeding was complete, the polymerization mixture was stirred for additional 30 min at 67° C. After a total of 4 hours polymerization time (3 hours 30 min feeding and 30 min stirring), 5 g of THF was added to the reactor and the polymerization mixture was cooled down to room temperature. Precipitation was carried out in 1.5 L of isopropyl alcohol. After filtration, the polymer was dried, re-dissolved in 96 g of THF, re-precipitated into 1.9 L of isopropyl alcohol, filtered, and dried in a vacuum oven at 45° C. for 48 hours to give 42.5 g (Mw=9,255 and Mw/Mn=1.67).

EXAMPLE 3

Photoresist Composition Without PAG of the Invention (Comparative)

2.780 g of the polymer formed as described above in Example 2 was dissolved in 24.225 g of propylene glycol monomethyl ether acetate (PGMEA), 24.225 g of cyclohexanone, and 48.450 g of methyl-2-hydroxyisobutyreate. To this mixture was added 0.281 g of triphenylsulfonium 1-((3-hydroxyadamantyl)methoxycarbonyl)difluoromethanesulfonate (as may be suitably prepared in Example 1 above), 0.035 g of 1-(tert-butoxycarbonyl)-4-hydroxypiperidine and 0.005 g of POLYFOX® PF-656 surfactant (Omnova Solutions Inc.). The resulting mixture was rolled on a roller for six hours and then filtered through a Teflon filter having a 0.2 micron pore size, thereby forming a positive-acting photoresist composition.

EXAMPLE 4

Photoresist with PAG of the Invention 2.724 g of the polymer formed as described above in Example 3 above was dissolved in 24.225 g of propylene glycol monomethyl ether acetate (PGMEA), 24.225 g of cyclohexanone, and 48.450 g of methyl-2-hydroxyisobutyreate. To this mixture was added 0.281 g of triphenylsulfonium 1-((3-hydroxyadamantyl)methoxycarbonyl)difluoromethanesulfonate (as may be suitably prepared in Example 1 above), 0.056 g of Synthesis of Triphenylsulfonium (1-pyrrolidonethoxycarbonyl)-difluoromethanesulfonate as prepared in Example 2 above (1.806% of a total solid weight), 0.035 g of 1-(tert-butoxycarbonyl)-4-hydroxypiperidine and 0.005 g of POLYFOX® PF-656 surfactant (Omnova Solutions Inc.). The resulting mixture was rolled on a roller for six hours and then filtered through a Teflon filter having a 0.2 micron pore size, thereby forming a positive-acting photoresist composition.

EXAMPLE 5

Lithography and Metorology 300 mm silicon wafers were spin-coated with an organic antireflective coating to form a first bottom antireflective coating (BARC) on a TEL CLEAN TRACK™ LITHIUS™ i+ coater/developer. The wafer was baked for 60 seconds at 215° C., yielding a first BARC film thickness of 75 nm. A second BARC layer was next coated over the first BARC, and the coated wafers were baked at 205° C. for 60 seconds to generate a 23 nm top BARC layer.

Photoresist compositions of Example 3 and 4 above were separately spin coated on top of the dual BARCs and softbaked at 120° C. for 60 seconds, resulting in a resist film thickness of 900 Å. The resist layer were coated with an organic topcoat layer and exposed at various doses from 19 to 59 mJ/cm² through a reticle having critical dimensions of 40 nm lines and spaces (L/S) at 80 nm pitch and 42 nm lines and spaces (L/S) at 84 nm pitch using an ASML TWINSCAN™ XT:1900i immersion scanner with a numerical aperture of 1.35 and dipole-35Y illumination (0.96 outer sigma/0.76 inner sigma) with X-polarization. The wafers were then post-exposure baked (PEB) at 125° C. for 60 seconds and developed for 12 seconds using a commercially 0.26N aqueous alkaline developer. The critical dimensions (CD) were measured with a Hitachi CG 4000 SEM.

EXAMPLE 6

Further Photoresist Preparation and Lithographic Processing

A photoresist of the invention is prepared by mixing the following components with amounts expressed as weight percent based on total weight of the resist compositions:

| Resist components | Amount (wt. %) |
| --- | --- |
| Resin binder | 15 |
| Photoacid generator | 4 |
| Ethyl lactate | 81 |

The resin binder is a terpolymer (2-methyl-2-adamantyl methacrylate/beta-hydroxy-gamma-butyrolactone methacrylate/cyano-norbornyl methacrylate. The photoacid generator is the compound TPS DHC-TFBS, as prepared in Example 1 above. Those resin and PAG components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetrabutylammonium hydroxide solution to develop the imaged resist layer.

What is claimed is:

1. A photoacid generator that comprises a structure of the following formula (I):

$$RO(C=O)(CXY)_p(CF_2)_nSO_3^- M^+ \qquad (I)$$

wherein R is non-hydrogen substituent that comprises a group of the structure —C(=O)N($R^1$)($R^2$) where $R^1$ and $R^2$ are each the same or different and may be hydrogen or a non-hydrogen substituent, or $R^1$ and $R^2$ may be taken together to form a ring with the nitrogen;

X and Y are each independently hydrogen or a non-hydrogen substituent;

p is 0 or a positive integer;

n is a positive integer; and

M+ is a counter ion.

2. The photoacid generator of claim 1 wherein $R^1$ and $R^2$ are independently selected from the group consisting of optionally substituted alkyl; optionally substituted C3-30 cycloalkyl, optionally substituted alkoxy, optionally substituted carbocyclic group, optionally substituted heteroalicyclic group that contains 1, 2 or 3 N, O and/or S ring atoms.

3. The photoacid generator of claim 1 wherein $R^1$ and $R^2$ are each other than hydrogen.

4. The photoacid generator of claim 1 wherein R is —(CXY)$_{1-10}$C(=O)N($R^1$)($R^2$) where each occurrence of X and Y is independently hydrogen or a non-hydrogen substituent.

5. A photoresist composition comprising a resin component and a photoacid generator of claim 1.

6. A photoresist composition comprising a resin component and a photoacid generator of claim 2.

7. A photoresist composition comprising a resin component and a photoacid generator of claim 3.

8. A photoresist composition comprising a resin component and a photoacid generator of claim 4.

9. A method for forming a photoresist relief image comprising:
   a) applying a coating layer of a photoresist composition of claim 5 on a substrate;
   (b) exposing the photoresist coating layer to patterned activating radiation and developing the exposed photoresist layer to provide a relief image.

10. A method for forming a photoresist relief image comprising:
    a) applying a coating layer of a photoresist composition of claim 6 on a substrate;
    (b) exposing the photoresist coating layer to patterned activating radiation and developing the exposed photoresist layer to provide a relief image.

11. A method for forming a photoresist relief image comprising:
    a) applying a coating layer of a photoresist composition of claim 7 on a substrate;
    (b) exposing the photoresist coating layer to patterned activating radiation and developing the exposed photoresist layer to provide a relief image.

12. A method for forming a photoresist relief image comprising:
    a) applying a coating layer of a photoresist composition of claim 8 on a substrate;
    (b) exposing the photoresist coating layer to patterned activating radiation and developing the exposed photoresist layer to provide a relief image.

13. A photoacid generator that comprises an anion component of any of the following Formula (I) through (XV):

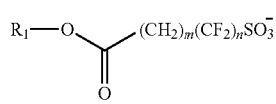
(I)

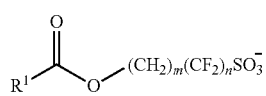
(II)

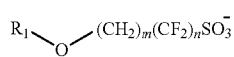
(III)

-continued

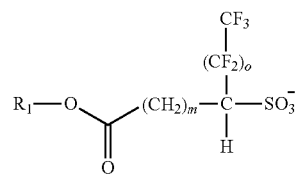
(IV)

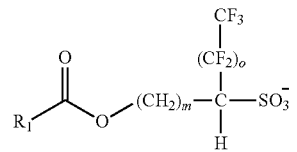
(V)

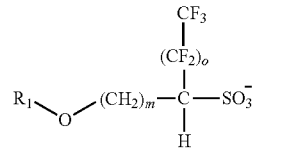
(VI)

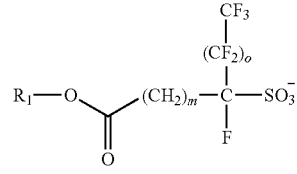
(VII)

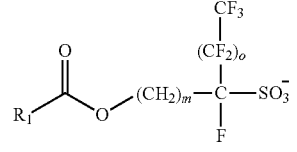
(VIII)

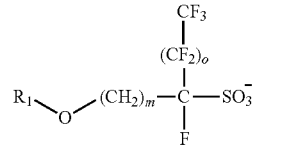
(IX)

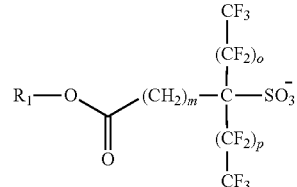
(X)

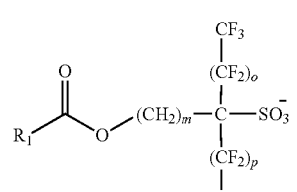
(XI)

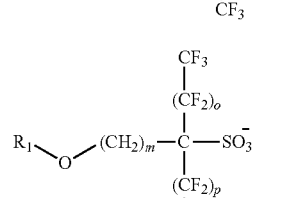
(XII)

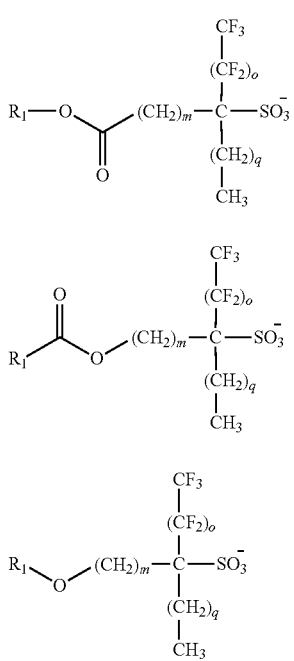

wherein in each of Formulae (I) to (XV):

m, n, o, p, q are independently an integer of 0 to 10;

R₁ is selected from one of (A), (B), (C), (D), (E), or (F) below:

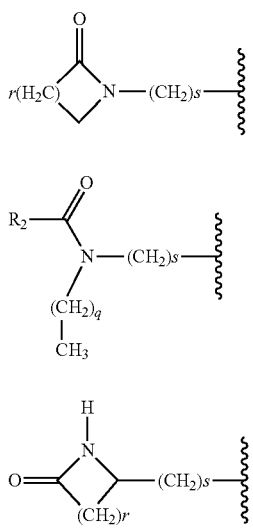

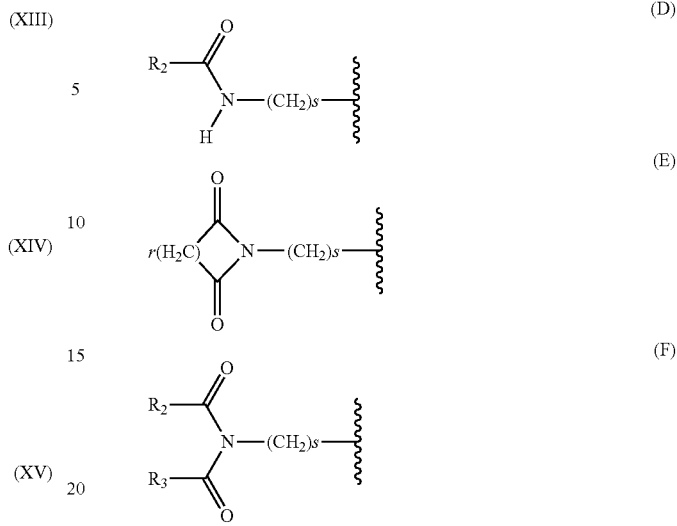

wherein:
R₂ and R₃ are the same or different optionally substituted branched, non-branched or cyclic aliphatic group;
q and r are independently an integer from 0 to 10; and
s is a positive integer from 1 to 10.

14. The photoacid generator of claim 13, wherein R₂ and R₃ are the same or different and are independently selected from the group consisting of optionally substituted C$_{1-30}$ alkyl, optionally substituted C$_{3-30}$ cycloalkyl, optionally substituted C$_{1-30}$ alkoxy, optionally substituted C$_{6-30}$ carbocyclic group, and optionally substituted C$_{3-30}$ heteroalicyclic group that contains 1, 2 or 3 N, O and/or S ring atoms.

15. The photoacid generator of claim 13 wherein the anion component is complexed with a sulfonium cation component.

16. The photoacid generator of claim 13 wherein the anion component is complexed with an iodonium cation component.

17. A photoresist composition comprising a resin component and a photoacid generator of claim 13.

18. A photoresist composition comprising a resin component and a photoacid generator of claim 14.

19. A method for forming a photoresist relief image comprising:
a) applying a coating layer of a photoresist composition of claim 17 on a substrate;
(b) exposing the photoresist coating layer to patterned activating radiation and developing the exposed photoresist layer to provide a relief image.

20. A method for forming a photoresist relief image comprising:
a) applying a coating layer of a photoresist composition of claim 18 on a substrate;
(b) exposing the photoresist coating layer to patterned activating radiation and developing the exposed photoresist layer to provide a relief image.

\* \* \* \* \*